United States Patent [19]

Helmer et al.

[11] Patent Number: 5,680,320

[45] Date of Patent: Oct. 21, 1997

[54] METHOD OF QUANTIFYING PERFORMANCE CHEMICALS IN PULP AND PAPER

[75] Inventors: Ulla Helmer, Solna; Lars Renberg, Västerhaninge; Ralf Olsson, Stockholm, all of Sweden

[73] Assignee: Eka Nobel AB, Bohus, Sweden

[21] Appl. No.: 444,053

[22] Filed: May 18, 1995

[30] Foreign Application Priority Data

May 18, 1994 [SE] Sweden ..................... 9401718

[51] Int. Cl.$^6$ .................................. G06F 19/00
[52] U.S. Cl. .................. 364/498; 364/499; 364/471.02; 364/571.02
[58] Field of Search ..................... 364/497–499, 364/571.01–571.05, 571.06–577, 581, 582, 469.01, 471.01, 471.02, 471.03; 356/312, 323, 325, 328; 250/339, 343, 353, 252.1

[56] References Cited

U.S. PATENT DOCUMENTS

| | | | |
|---|---|---|---|
| 4,627,014 | 12/1986 | Lo et al. ............................ | 364/571 |
| 5,104,485 | 4/1992 | Weyer . | |
| 5,121,337 | 6/1992 | Brown . | |
| 5,206,701 | 4/1993 | Taylor et al. . | |
| 5,223,715 | 6/1993 | Taylor ........................... | 250/343 |
| 5,242,602 | 9/1993 | Richardson et al. . | |
| 5,243,546 | 9/1993 | Maggard ......................... | 364/571.02 |
| 5,360,972 | 11/1994 | DiFoggio et al. ................ | 250/343 |

OTHER PUBLICATIONS

S.D. Brown, "Chemometrics", Anal. Chem. 62, pp. 84R–101R (1990).

Pulp characterization using spectroscopy and multi-variate data analysis, L. Wallbäcks, Dept. of Organic Chemistry, Univ. of Umeå, Sweden (1991).

Research Disclosure, Method of Measurement of Chemicals in Paper, Dec. 1992/945.

Abstract of Research Disclosure 344066 by Hercules Incorporated date unknown.

*Primary Examiner*—James P. Trammell
*Attorney, Agent, or Firm*—Burns, Doane, Swecker & Mathis, L.L.P.

[57] ABSTRACT

A method is provided for quantifying the amounts of performance chemicals selected from the group consisting of wet strength agents, starches and retention agents, hydrophobic agents and debonding agents, reacted or retained with the cellulose fibers in fluff pulp or paper. The method comprises (I) developing a calibration model by (I.a) registering absorption, reflectance or emission spectral raw data of reference samples of paper or pulp containing known amounts of the performance chemicals to develop a learning set; (I.b) processing the spectral raw data from the registered spectra to reduce noise and adjust for drift and diffuse light scatter; (I.c) performing a data analysis on the learning set in which the processed spectral data of the reference samples are transferred into latent variables based on principal component analysis, and applying chemometric techniques on the latent variables in order to find the mathematical expression of the calibration model; and (II) registering absorption, reflectance or emission spectral raw data of a sample of fluff paper or pulp containing unknown amounts of chemicals, processing the spectral raw data as according to (I.b); transferring the processed spectral data into latent variables as according to (I.c), and applying the developed calibration model on the latent variables in order to determine the unknown amounts of the reacted or retained performance chemicals.

15 Claims, 5 Drawing Sheets

METHOD OF QUANTIFYING PERFORMANCE CHEMICALS IN PULP AND PAPER

FIELD OF THE INVENTION

The amounts of reacted and/or retained performance chemicals in pulp and paper cannot today be analysed in the paper machine but must be tested off-line or sent to laboratories skilled in the art of analysing the chemicals.

The present invention is directed to a method for quantitative determination of reacted and/or retained paper chemicals selected from the group consisting of wet strength agents, starches and retention agents, hydrophobic agents and debonding agents in pulp and paper, and more particularly to a method for the direct and continuous analysis of the amounts of paper chemicals in paper containing, e.g. wet strength agents, starches and retention agents; hydrophobic agents, such as alkyl ketene dimer (AKD), alkylene succinic anhydride (ASA), carbamoylchloride and rosin; and debonding agents (fluff chemicals) such as e.g. quaternary fatty amines and fatty amine oxides.

BACKGROUND OF THE INVENTION

For a number of paper applications the amounts of chemicals as reacted and/or retained amounts are of fundamental importance, examples being that of papers of tissue quality, as well as paper-bags and paper-sacks, printing qualities and paper board.

The amounts of chemicals reacted and/or retained in pulp and paper are determined by different analytical methods. Some of the methods are standardized, such as the determination of rosin according to the TAPPI method T 408 om-82 and nitrogen according to Kjeldahl (see p. 6). AKD can be analysed according to the method proposed by P. Dart et al (see p. 7). All these methods are rather time consuming and can take days.

One major drawback with those methods of determination is this delay between a change in a parameter in the manufacturing of a paper and the answer of the determination of the reacted and/or retained amounts of performance chemicals in pulp and/or paper. This delay may lead to important losses of paper in case the reacted and/or retained amounts prove to be inadequate since, by the time this assessment has been accomplished, there may be very large quantities of paper of these inadequate amounts produced.

It is obvious that the methods of determination of these amounts presently in use in the paper production industry are drawbacks to the productivity and economy of the paper production process. Thus, there is a definite need for more convenient methods of quantifying the reacted and/or retained amounts of performance chemicals within the paper manufacturing industry.

The present invention has for object to offer a solution to said problem, by providing a method that allows the quantification of said chemicals in the paper and/or pulp during the production process. This object is attained by the combined use of spectrometric and chemometric techniques.

According to the invention, the paper or the pulp in or from the production line is submitted to spectrometric analysis. However, the pulp as well as the paper represents a multi-component system or a system having a high degree of background interferences which increases the problems of spectrometric analysis.

The use of multivariate data analysis in the characterization of multi-component systems is presently a field of development. Applied generally to the field of chemistry, and particularly to the field of analytical chemistry, those several statistical methods also are termed chemometric methods, forming the discipline of chemometrics. The technique of chemometrics is more fully explained in S. D. Brown, "Chemometrics", Anal. Chem. 62, 84R-101R (1990), which by reference is incorporated herein in its entirety.

An example of the use of chemometrics is given in the thesis of Wallbäcks (Pulp characterization using spectroscopy and multi-variate data analysis, L. Wallbäcks, Dept. of Organic Chemistry, Univ. of Umeå, Sweden (1991)), who has shown that multivariate data analysis can be used to predict various physical properties as a function of the initial characteristics of the unbeaten pulp and the effect of beating.

Further, Brown et al, in the U.S. Pat. No. 5,121,337 (1990) disclose a method, based on multivariate data analysis, for correcting spectral data for data due to the spectral measurement process itself and estimating unknown property and/or composition data of a sample using such method.

On the other hand, Richardson et al, in U.S. Pat. No. 5,242,602 disclose a method for simultaneously measuring the concentration of multiple chemical components, which they call performance indicators, in an aqueous system, by the analysis of the spectrum of the aqueous system in the wavelength range 200 to 2500 nm and by applying chemometric algorithms to the spectrum to simultaneously determine the concentrations of the different performance indicators.

Weyer, U.S. Pat. No. 5,104,485 discloses a method for measuring extremely low concentrations of non-aqueous constituents or chemicals in a water/matrix, including differentiating between pulp fines and extremely low concentrations of individual chemicals in a water/cellulose matrix such as occur in papermaking. The water/matrix is exposed to the near-infrared spectrum from 1000 to 2500 nm to produce a record voltage that is directly proportional to the absorption by the non-aqueous constituent. The amount non-aqueous constituent is determined from voltage values of incremental additions of the non-aqueous constituent.

In addition Hercules reported in a research disclosure (December 1992/945) that in the papermaking process, a water/cellulose mixture is laid on a wire screen and the water is filtered off leaving the fibers and various additives. The paper sheet produced is composed of cellulose fibers, fillers such as clay and calcium carbonate, and additives such as optical brighteners, sizes, and wet and dry strength resins. Various instrumental systems are available for measuring some of these constituents such as the clay. These systems, however, are limited in the determinations that can be carried out.

A method for determining several individual chemical constituents simultaneously in a paper sheet has been developed. Radiation from a near infrared sourse is allowed to impinge upon the paper sheet, and after interaction of the radiation with the chemical constituents in the sheet, the reflected radiation is collected and stored. The chemical composition is calculated from the stored data after mathematical treatments are applied. The measurement system is calibrated via samples of known composition. Use of the full near infrared spectrum from 1100 to 2500 nanometers permits the analysis of several constitents simultaneously, especially when derivatives are employed as part of the mathematical treatment. This analysis aids in determining the extent of retention of the chemical additives and fillers.

However, the present inventors have shown that four steps should be involved for a useful quantification of a chemical on the basis of spectroscopy. The first step is recording the simultaneously determination of the emission, transmittance or reflectance values from a huge number of wave lengths (e.g. 300 to 600 numbers of wave length is not uncommon). The second step is a pre-treatment of the spectral data, which is essential in the NIR region (800–2400 nm). The third step is transformation of data, usually by centring, normalisation or autoscaling the data. The forth step is to find the mathematical expression for the calibration function.

The description of the method according to Hercules only disclose the first and second step. The spectral information is collected, followed by an undefined mathematical treatment. The only detail that is given is the application of derivatives (which is a commonly used technique within spectroscopy). Nothing is revealed about the numerical algorithm used for the transformation of data and algorithm for calibration. This step is of utmost importance for a useful quantification of a chemical on the basis of spectroscopy.

However, according to this invention specific algorithms are applied to overcome especially two disadvantages, namely:

1. The number of wave lengths can be considerable and outnumbers the number of samples, used for the calibration. As an example, if the reflectance of 300 wavelength are recorded for 20 samples, with conventional mathematical models only the values from the number of samples minus 2 can be used for the calibration. Thus, in this case only values from 20−2=18 wave lengths can be used and the information from the other 282 wave lengths cannot be taken into account. According to this invention all spectral information is used and compiled by transferring all the information recorded into so called latent variables based on principal component analysis.

2. The spectral information is often highly correlated which seriously affect the success for quantification. If the spectral information is transferred into latent variables by principal component analysis a higher degree of orthogonalisation is obtained which can be a crucial factor for success.

Moreover, none of the above mentioned authors suggests how to solve the problem of determining the amounts of chemicals present in a paper in a paper production process in a way permitting the monitoring of these parameters and no details of the calibration procedures are given. It should be emphazised that the expression "determination" in this context can be interpreted either as a qualitative analysis or as a quantitative analysis. A qualitative analysis is the determination of the presence of a chemical while quantitativ analysis relates to the estimation of a certain value, including the degree of uncertainty of this value (expressed in statistical terms such as confidence interval etc.).

The object of the present invention is to provide a reliable and precise way of monitoring—i.e quantification—the amounts of chemicals present in a paper by spectroscopic measurement in combination with multivariate data analysis using chemometrical techniques.

The object of the invention thus is to provide a method for determination of the above-mentioned chemical additives in pulp and paper in real time without the use of the traditional lengthy analytical methods.

It is another object of the invention to provide a method of maintaining an effective process control programme wherein the above-mentioned chemicals are quantified to detect any change and provide control input, assuring optimum dosage levels for the different chemical additives.

Yet another object is a means of maintaining an effective process control programme wherein the reacted and/or retained amounts of performance chemicals are quantified to detect any changes thereof and provide control input, assuring optimum dosage levels of performance chemicals, by the use of a method as defined above.

The methods and means as disclosed according to the invention are those as further defined in the claims.

The invention relates to the determination of the reacted and/or retained amounts of chemicals such as wet strength agents, starches and retention agents; hydrophobic agents, such as alkyl ketene dimer (AKD), alkylene succinic anhydride (ASA), alkyl carbamoyl chloride and rosin; and debonding agents (fluff chemicals) such as quaternary fatty amines and fatty amine oxides needed for adequate pulp and paper making.

Wet strength additives are e.g. urea-formaldehyd-resins (UF), melamine-formaldehyde (MF), and polyamide-amine-epichlorohydrine resins (PAAE). They are water-soluble polymers and are added to the stock as solutions. They crosslink further during the drying of the paper and impart wet strength to the paper.

Dry defibration of cellulose pulp gives a cotton like soft material, fluff, used in absorbing sanitary products such as diapers etc. The pulp product intended for use for dry defibration has to be treated with debonding agents which contain both hydrophobic and hydrophilic groups. The hydrophilic group will increase the absorption speed and capacity in the final product and counteract the hydrophobicity rendered by the hydrophobic groups.

Pulp and paper obtain strength from the interfibrillar hydrogen bonds which are created when the cellulose fibres are drawn together by surface tension during the drying process. The interfibrillar hydrogen bonds should be as few as possible in the pulp intended for fluff. The most common debonding agents are the quaternary ammonium type, with hydrophobic, long chain, alkyl substituent groups such as those, preferably, stemming from tallow and stearic acid. The big hydrophobic groups interfere with and prevent the formation of hydrogen bonds.

The hydrophilic groups comprise quaternary ammonium groups and amino oxides.

The fluff pulp is produced on a paper machine as a thick paper and the debonding agents are added to the stock as ordinary paper chemicals.

Nearly all starches used in the paper production process for retention or dry strength are cationic.

Debonding agents, wet-strength agents, cationic starches and retention agents contain nitrogen. The amount of nitrogen is determined e.g. for the calculation of the retention of said chemicals. One important aspect in the papermaking industry is therefor to quantify the nitrogen retention in pulp and paper. The main reason for nitrogen in paper chemicals is that the nitrogen atom renders the molecule a cationic charge. Since the cellulosic fibre is negatively charged this will lead to retention of the chemical. The retained amount of nitrogen containing chemicals is hitherto determined with the well known Kjeldahl nitrogen method (J. Kjeldahl, Z. anal Chem 22, 366 (1983).

One obvious drawback with this way of controlling the retention of nitrogen is the delay between the production of a paper and the assessment of the value for the retention of nitrogen in that paper. This may lead to important losses of paper in case retention of the actual nitrogen containing chemical proves to be inadequate since by the time this assessment has been accomplished there may be very important amounts of paper of this inadequate quality produced.

Sizing is the process carried out to produce paper or board that has an enhanced resistance to penetration by liquids such as water and printing inks. Sizing chemicals are rosin, alkyl carbamoyl chloride, alkyl ketene dimer (AKD) and alkenyl succinic anhydride (ASA). Rosin, which consists of a mixture of rosin acids such as abietic acid, is prior to the present invention, analysed according to TAPPI T 408 om-82. Alkyl ketene dimer (AKD) is a neutral sizing agent that is now widely used. The AKD reacts with cellulose giving an ester bond. Infrared (IR) and nuclear magnetic resonance spectrometry (NMR), calorimetric and solvent extraction studies have been presented to support the above mechanism. Little detailed work has been reported on the quantitative analysis of AKD in paper and waste waters. Hydrolysis of AKD gives the corresponding ketone. The determination of the ketone by high-performance liquid chromatography (HPLC) with a refractive index detector has been reported, and its determination by IR spectrometry has also been investigated. Although simple tests for water absorption of paper are performed readily, knowledge of the AKD content is still important for adequate paper-making. To minimise production costs, the determination of the distribution of AKD in the paper and the white water can indicate ways in which the sizing agent is lost. Further, the amounts of AKD retained in paper, together with "cure promoter" chemicals, can influence the storage time required for the paper to achieve a sufficient degree of sizing. [Analyst. January 1990, vol. 115, Determination of Alkylketene Dimer Sizing Agent Products in Paper by Capillary Gas Chromatography, Peter J. Dart, Albright and Wilson, Avonmouth Works, Bristol BS11 OYT, UK and David V. McCalley, Department of Science, Bristol Polytechnic, Frenchay, Bristol BS16 10Y, UK].

Alkenyl succinic anhydride, ASA, is a very reactive hydrophobic substance. The ASA molecule comprises a long hydrophobic group in the form of an olefin, attached to a succinic anhydride. The anhydride has to chemically react with the fibre/fines surfaces. The ASA molecule is non-ionic and is insoluble in water but can be emulsified with the help of cationic starch or polymers. The fine cationic microscopic droplets are retained by the fibre/fines and are broken when the temperature is increased. The single ASA molecule react with an OH-group on the surface and the final paper becomes hydrophobic. The analysis of reacted and/or retained amounts of ASA are just as difficult as it is to analyse AKD. The analyses as used today are not standardised and rather uncertain. Thus, a more convenient and faster method is highly required.

SUMMARY OF THE INVENTION

The above objects of the invention are obtained by a method of quantifying the amounts of reacted and/or retained chemical additives in paper by analysing the visible, near-infrared and/or infrared spectrum of the paper/pulp in the process line in a wavelength range within 400 nm to 400 µm, and applying chemometric evaluation of the spectrum to quantify the amounts of reacted and/or retained chemical additives of the paper.

DETAILED DESCRIPTION OF THE INVENTION

According to the invention it has now, by an extensive development work, been shown that it is possible to monitor the absorption, reflectance and emission spectra of pulp and paper using an UV-VIS-NIR and/or IR spectrometer and, by the use of absorbance, reflectance or transmittance values at discrete wavelengths from these spectra, quantify the above defined chemicals in the corresponding paper.

The terminology pulp and/or paper as used herein refers not only to bleached pulp and/or paper, but also to unbleached or partially bleached pulp and/or paper as well as filled or unfilled qualities. This includes sac paper, liner, liquid board, printing paper and the like as well as creped paper qualities and fluff pulp.

Technically, the spectrometric analysis can be carried out as a monitoring process by use of an on-line, in-line or at-line probe, or by taking individual samples for separate analysis (off-line). In both cases, the emission, transmittance or reflectance spectra are subject to further data treatment using values from several discrete wavelengths from each particular spectrum.

An example of such a technique is the use of a device, placed at a distance from the process, containing a light source, detector, electronic components and other necessary components to transmit a signal through an optical fibre to the sample, where the light is transmitted through or reflected on or partly through the sample. The resulting signals are returned to the detector in an accompanying optical fibre cable, and recorded.

In the spectrometer, the light is converted into an electric signal which is then conveyed to a computer where the spectrum of a previously stored reference scan can be related to, e.g. subtracted from, the sample spectrum and a reference corrected spectrum is calculated.

Another example is by manually or automatically taking samples at relevant time intervals and submitting the samples to analysis in an analytical instrument, containing the light source, detector, electronic components and other necessary components. The emission, transmittance or reflectance spectra are then subjected to further data treatment, using values from several discrete wavelengths from each particular spectrum.

The detection is performed in the UV-VIS-NIR wavelength range of 200 nm to 2500 nm preferably 800 nm to 2500 nm and/or the IR wavelength range of 2500 nm to 400 µm. This can be accomplished by the use of a scanning instrument, a diode array instrument, a Fourier transform instrument or any other similar equipment, known to the man skilled in the art.

It is preferred that the detector have a measuring interval of at least 10 nm, preferably 2 nm, and most preferably 1 nm or less.

An evaluation of wavelengths which contain absorption, reflectance or emission provides features relevant for the analysis. By way of the application of chemometrical methods to the obtained spectra it is then possible to ignore wavelengths which do not contain information that contribute to the chemical analysis, even though the measurement will include information from the entire wavelength range.

The determination and control of the reacted and/or retained chemical additives of paper in pulp and/or paper by use of the spectrometric measurements comprise three main stages, the first main stage being the development of a calibration model, involving the stages development of learning sets; data processing; and data analysis, by use of pulp and/or paper samples of known amounts of chemicals; and the second main stage being that of the spectrometric analysis of the sample of the unknown amounts of chemicals, spectral data processing, optionally followed by data analysis; and application of the calibration model, developed in the first main stage, to the thereby obtained data.

(I) DEVELOPMENT OF A CALIBRATION MODEL

The amounts of the reacted and/or retained chemical to be determined are measured in the traditional analytical way for a number of pulp and/or paper samples. These samples, characterized by traditionally analysed amounts, then are used in the development of a calibration model wherein the three substeps mentioned above are applied to the registered absorption, reflectance or emission spectra of said samples.

(I.a) Development of learning sets

Model learning sets consist of a large number of absorption, reflectance or emission spectra from the samples with known characteristics, which samples preferably should be representative of the production line. The learning sets are used in the chemometric algorithms to calculate the resulting model parameters.

(I.b) Data processing

To reduce noise and adjust for base line drift the spectral raw data should be processed. This processing may also reveal hidden information, such as identity of apparently dissimilar spectra or non-identity of apparently very similar spectra.

Moreover, the assumptions leading to Beer's law (stating that, for a given absorption coefficient and length of the optical path in the absorptive media, the total amount of light absorbed is proportional to the molecular concentration of the sample) are usually not fulfilled in the complex system that constitutes the pulp or paper. This is mostly due to light scatter variation depending on the physical dimensions of the sample.

Various theories have been developed to overcome this problem and the most used are:

1) The Kubelka-Munk transform (P. Kubelka, F. Munk, Z. Tech. Physik 12, 593 (1931)), which takes account of absorption and scatter, is according to Eq. 1:

$$A_{ik} = \frac{(1-R_{ik})^2}{2R_{ik}} \quad (1)$$

where $R_{ik}$ is the apparent absorbance at the wavelength k, $A_{ik}$ is the transformed absorbance at the wavelength k, and the index i represents the sample spectra available.

2) The Multiplicative Scatter Correction (MSC) (P. Geladi, D. MacDougall, H. Martens, Appl. Spect. 39, 491–500 (1985)) where each spectrum is 'corrected' in both offset and slope by comparing it to an 'ideal' spectrum (the mean spectrum), is according to Eq. 2:

$$A_{ik} = \frac{R_{ik} - \hat{a}_i}{\hat{b}_i} \quad (2)$$

where $A_{ik}$, $R_{ik}$, i and k have the same meanings as above, $\hat{a}_i$ is the least squares estimation of the intercept parameter, and $\hat{b}_i$ is the least squares estimation of the slope parameter.

3) The use of derivatives, e.g. up to the fourth order derivatives (A. Savitzky, M. J. E. Golay, Anal. Chem. 36, 1627–1639 (1964)). The derivative of the spectrum results in a transformed spectrum, consisting only of the relative changes between the adjacent wavelengths, and it has been shown that the peak intensities of derived spectra tend to be more linear with concentration (T. C. O'Haver, T. Begley, Anal. Chem. 53, 1876 (1981)).

4) The use of the Fourier transformation, or by use of the Standard Normal Variate transformation as disclosed in R. J. Barnes, M. S. Dhanoa and S. J. Lister, Appl. Spectrosc., Vol. 43, number 5, pp. 772–777 (1989).

(I.c) Data analysis

Data analysis using chemometric techniques then allows the calibration model to be developed. There are several chemometric techniques which can be used, such as Principal Component Analysis (PCA), Partial Least Squares Regression (PLS), Principal Components Regression (PCR), Multilinear Regression Analysis (MLR) and Discriminant Analysis. The preferred chemometric technique according to the invention is the PLS method.

(I.c.1) Principal Component Analysis (PCA)

By PCA, a set of correlated variables is compressed into a smaller set of uncorrelated variables.

This transformation consists of a rotation of the coordinate system, resulting in the alignment of information on a fewer number of axes than in the original arrangement. Hereby, the variables that are highly correlated with one another will be treated as a single entity. By using PCA, it thus will be possible to obtain a small set of uncorrelated variables still representing most of the information which was present in the original set of variables, but being far easier to use in models.

In general, 2 to 15 principal components will account for 85% to 98% of the variance of the variables.

(I.c.2) Partial Least Squares Regression (PLS)

PLS is a modelling and computational method by which quantitative relations can be established between blocks of variables, e.g. a block of descriptor data (spectrum) for a series of samples and a block of response data measured on these samples. By the quantitative relation between the blocks, it is possible to enter spectral data for a new sample to the descriptor block and make predictions of the expected responses. One great advantage of the method is that the results can be evaluated graphically, by different plots. In most cases, visual interpretations of the plot are sufficient to obtain a good understanding of different relations between the variables. The method is based upon projections, similar to PCA. The PLS method is detailedly disclosed in Carlsson R., Design and optimization in organic synthesis, B. G. M. Vandeginste, O. M. Kvalheim, Eds., Data handling in science and technology (Elsevier, 1992), vol. 8.

(I.c.3) Principal Components Regression (PCR)

PCR is closely related to PCA and PLS. As in PLS, each object in the descriptor block is projected onto a lower dimensional space yielding in scores and loadings. The scores are then regressed against the response block in a least squares procedure leading to a regression model which can be used to predict unknown samples. The same model statistics as in PLS and PCA can be used to validate the model.

For an exellent tutorial in PCA, PLS and PCR, see P. Geladi et al in "Partial Least-Squares Regression: A Tutorial" in Anal. Chim. Acta, 185, 1–32 (1986), which is incorporated herein by reference in its entirety.

(I.c.4) Multilinear Regression Analysis (MLR)

By MLR, the best fitting plane for a parameter as a function of the spectra is defined, using least squares techniques to define each boundary of the plane. This plane then is used to recognize and assign a predicted value to an unknown parameter.

This technique is generally limited to relatively 'clean' systems where there is not a significant amount of matrix interference and, in contrast to PLS, it requires more objects than variables.

(I.c.5) Discriminant Analysis

This is a method whereby, by use of spectral data, the known parameters are grouped into different clusters, separated by linear decision boundaries.

From its spectrum, a sample of unknown parameters then can be matched to a cluster, and the parameters can be assigned a value, e.g. the average value of the cluster.

This is a very useful technique for quality screening, but requires a very large data base to obtain statistically significant results.

(II) DETERMINATION OF THE UNKNOWN CHEMICALS BY APPLICATION OF THE CALIBRATION MODEL

Once a calibration model has been developed, the determination of the unknown amounts of each chemical can be performed by registering the absorption, reflectance or emission spectrum, in correspondence to (I.a). The processing of the thereby obtained spectral raw data as according to (I.b); optionally performing a data analysis on the processed spectral data as according to (I.c); and applying the developed calibration model to the thereby obtained data.

The invention will now be illustrated by way of examples.

EXAMPLE

Diffuse reflectance near-infrared spectrometry (NIRR) of the paper sample, linearisation of spectral data and multivariate data evaluation using the PLS-algorithm were used to determine the amounts of nitrogen, the amounts of reacted and/or retained AKD and rosin.

EXAMPLES OF DEVELOPMENT OF A CALIBRATION MODEL (A) Development of learning sets

SAMPLES

The reference paper samples consisted of in total 57 paper sheets of different paper qualities of bleached and unbleached pulp, 20 of bleached pulp and 37 of unbleached pulp, the latter being of both creped and uncreped qualities:

- samples made in a Laboratory Dynamic Sheet Former, from hardwood 35° SR, grammage 70 g/m$^2$;
- samples made on a pilot paper machine, from bleached craft pulp (50/50 softwood-hardwood) 35°–39° SR, grammage 70 g/m$^2$;
- samples of both ordinary and creped (crepe grade 3%) qualities from unbleached craft pulp with 30–40% recycled fibres, 20°–25° SR, varying porosity 14.1–17.4 Gurley sec, grammage 70 g/m$^2$, density 600 kg/m$^3$;
- samples from different paper mills, such as liner of hardwood, grammage 160–180 g/m$^2$.

All of the above samples were scanned by NIRR and models were developed.

Figure 1:
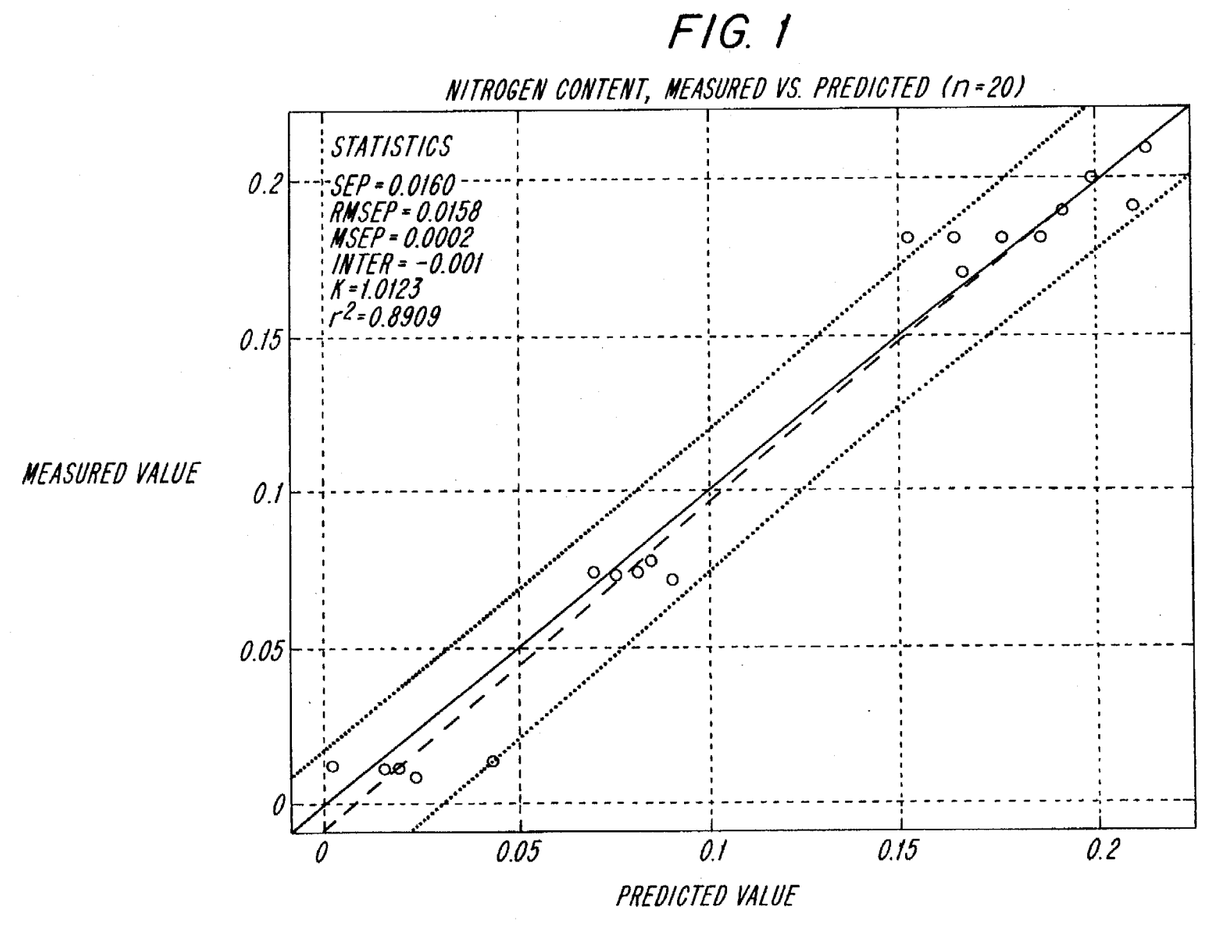
Figure 2:
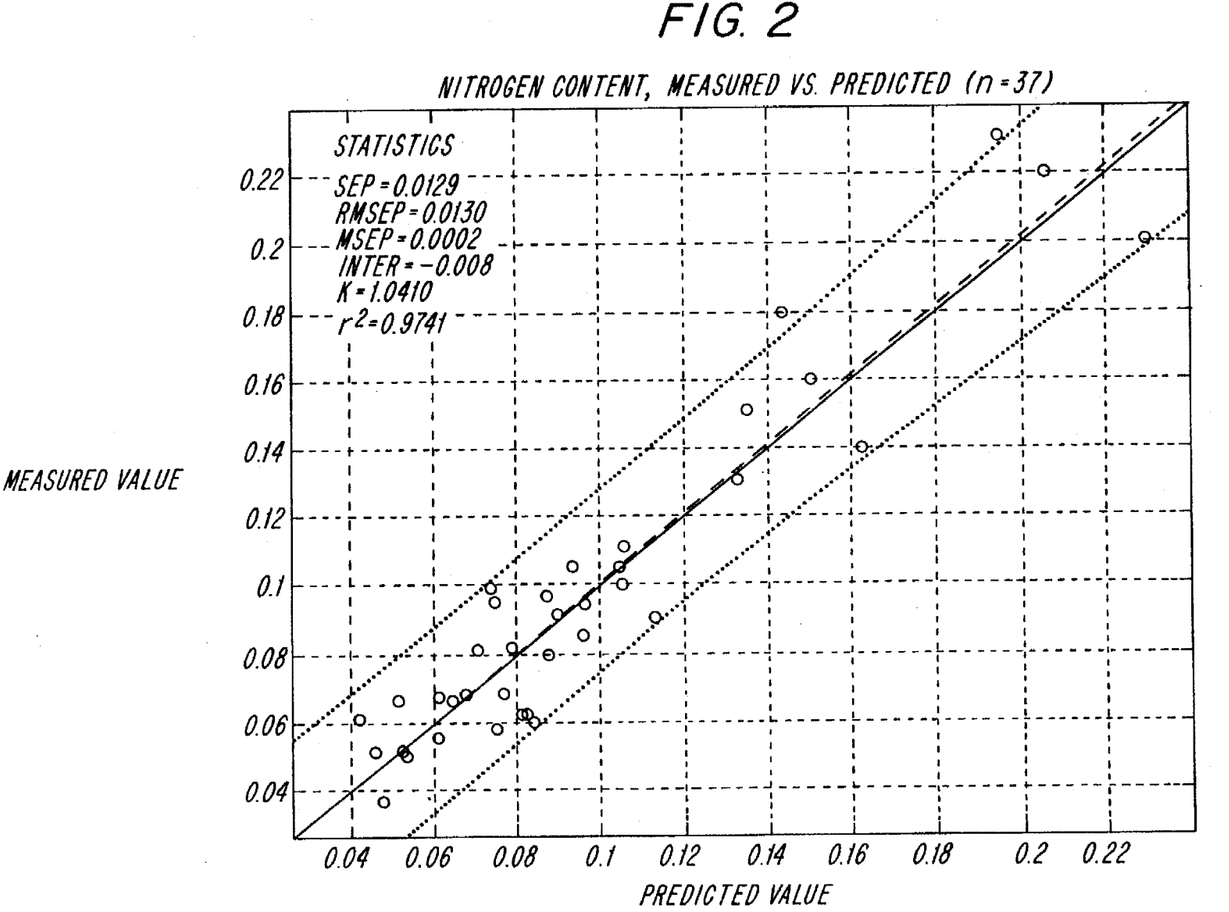

The paper samples had been subjected to treatment with nitrogen containing additives and the results can be seen in FIGS. 1–2.

Paper samples containing UF-resin were produced at an experimental paper machine with the following experimental parameters:

Pulp: unbleached hardwood, sulphate, 32° SR
Chemicals: UF-resin, added amount 0 to 3% dry weight on dry fibre and alum 1,5%, pH=4,5 ($H_2SO_4$), resulting in 51 samples
Temperature: 20° C.
Grammage: 70 g/m$^2$
Machine: system closed.
Press sect.: 1) 4 bar, 2) 1 bar
Drying section: 60°/80°/95°/110° C.
Tests: $N_2$- analysis The 51 samples were analysed on nitrogen content according to Kjeldahl and scanned by NIRR. A model was developed and can be seen as FIG. 3.

The same procedure was also used on different numbers of paper samples treated with and tested for total and reacted AKD.

Paper samples containing alkyl ketene dimer, AKD, were collected from different paper mills. The 46 samples were produced of different bleached pulp qualities and some had calcium carbonate as filler. All the samples on were analysed on total and reacted AKD according to the procedure developed by P. Dart et al., (see p.7) and then scanned by NIRR. Models were developed and the results can be seen in FIG. 4 (for total amount) and FIG. 5 (for reacted amount).

The same scanning was also used on different numbers of paper samples treated with and tested for the retention of rosin, as reported in Table I.

TABLE I

| DE-SCRIP-TOR | RA2 | SEP | MSEP | RMSEP | #PC:S | RSDb (%) | RSDw (%) |
|---|---|---|---|---|---|---|---|
| Retained amount rosin | 0.946 | 0.031 | 0.001 | 0.003 | 9 | — | 1.59 |

The paper samples containing rosin were produced at an experimental paper machine with the following experimental parameters.

Pulp: bleached hardwood 30%, 35% Birch and 35% Beech, 2% alum., $H_2SO_4$, pH=4.5, resulting in 31 samples.
Chemicals: Rosin dispersion added amount 0 to 1,0% dry weight on dry fibre
Addition order: alum, rosin
Temperature: 20° C.
Grammage: 70 g/m$^2$
Machine: system closed.
Press sect.: 1) 4 bar, 2) 1 bar
Drying section: 60/80/95/110
Test: Analysis of rosin All the 31 samples were analysed according to TAPPI T 408 OM-82 on the content of rosin.

NEAR INFRARED REFLECTANCE (NIRR) MEASUREMENTS

The NIRR measurements were obtained using a NIR Systems® 6500 spectrometer, from NIR systems, U.S., equipped with a High fat/moisture cell with a scan surface of up to 60 cm$^2$, with a spectral operating range between 400 nm and 2500 nm, in even intervals of 2 nm, yielding 1050 measurements at different wavelengths. Diffuse reflectance data were obtained as apparent absorbance, and transferred to a Macintosh® Quadra 700 computer.

(B) Data processing

The spectral data matrix was reduced to the NIR region (1100–2500 nm) for greater modelling speed. The spectra were reduced by a factor of 8 (every eighth wavelength was kept), which resulted in 175 spectral points for modelling.

LINEARISING TRANSFORMATION

The best linearising function was established using a factorial design approach (R. J. O. Olsson, in Near Infra-Red Spectroscopy, I. T. Hildum, K. L. Naes T. and Tandberg A., Eds. Ellis Horwood Limited, Chichester, (1992) pp.103–107) and was found to be the MSC with mean spectrum subtraction and incorporating the calculated intercept and slope parameters in the independent dataset (spectra).

The Mean Squared Error Prediction (MSEP) (H. Martens, T. Naes, Appl. Spect. 39, 491–500 (1985)) according to Eq. 3 herein below was evaluated as a number of latent variables kept in the PLS model. The linearising function/functions that yielded the smallest MSEP for the different descriptors then was used in the subsequent PLS modelling.

$$MSEP = \frac{1}{n} \sum_{i=1}^{n} (\hat{c}_i - c_i)^2 \qquad (3)$$

n is the number of samples, $\hat{c}_i$ is the modelled descriptor value and $c_i$ is the traditionally measured descriptor value. The index i is the descriptor of the sample i.

(Other statistical parameters related to MSEP are the Standard Error Prediction (SEP) and the Root Mean Squared Error Prediction (RMSEP), given herein below by Eqs. 4 and 5, respectively.)

(C) Data analysis

The MATLAB software V 3.5 was used for numerical calculations. The PLS-algorithm used for modelling the relationships between the spectra and descriptors is a customised function in the commercially available 'Chemometrics Toolbox' based on the NIPALS algorithm (H. Wold, P. Krishnaiah, Multivariate Analysis, 391 (1966)). The convergence criteria for the algorithm were $1 \times 10^{-10}$ or 100 iterations. The method of establishing the significant number of PLS-components was crossvalidation (S. Wold, Technometrics 20, 397–405 (1978)) (Jack-knifing) with one sample left out. This number here was found to be 15 for both the bleached and the unbleached paper samples. The values were mean-centered and scaled to unit variance prior to modelling (autoscaling or z-transform) and rescaled prior to model evaluation.

RESULTS

The measured vs. modelled values of the amounts of chemicals of the different paper qualities are plotted in FIGS. 1 to 5 respectively, with a 95% t-test confidence interval for the, to the data, least squares fitted line.

Figure 3:
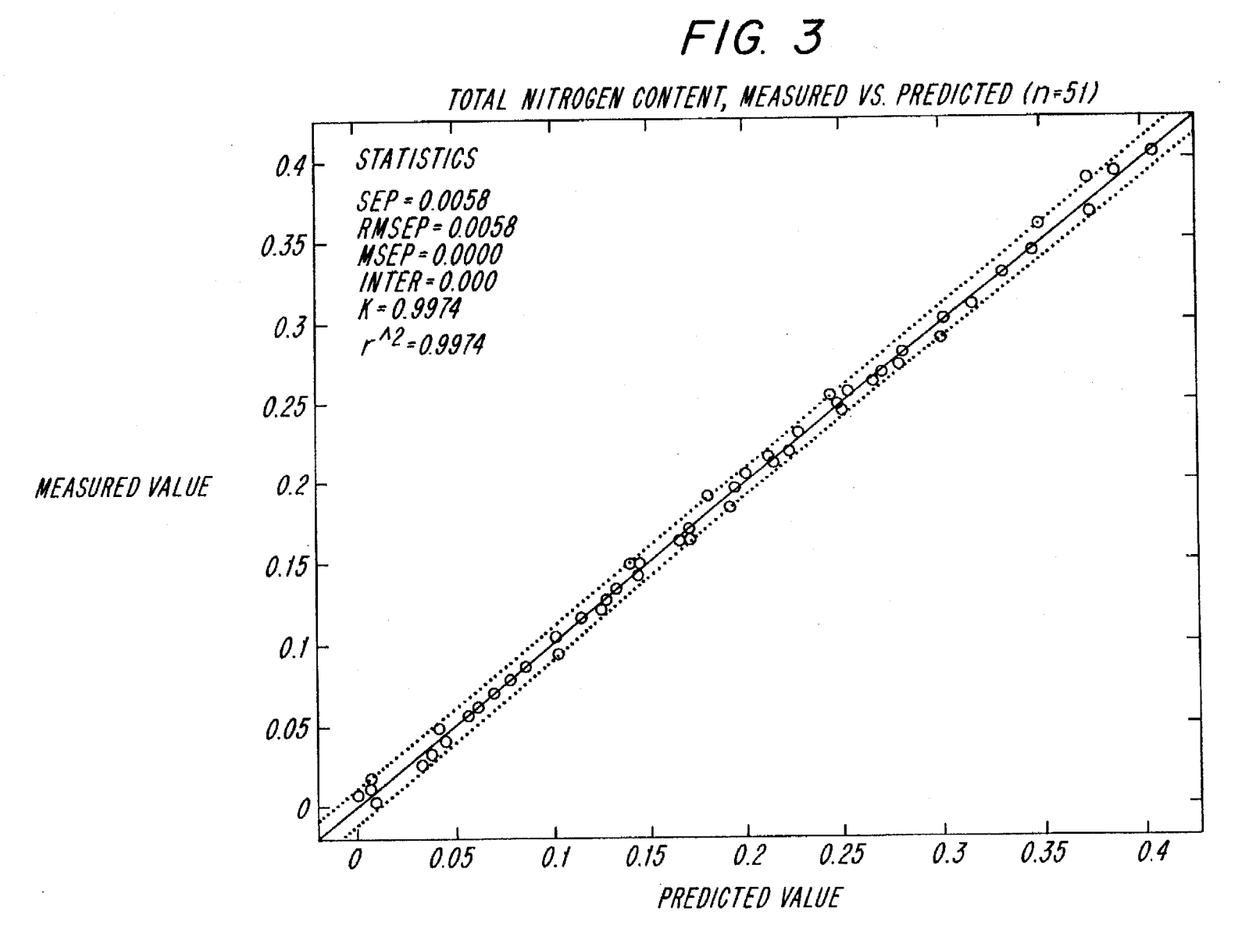
Figure 4:
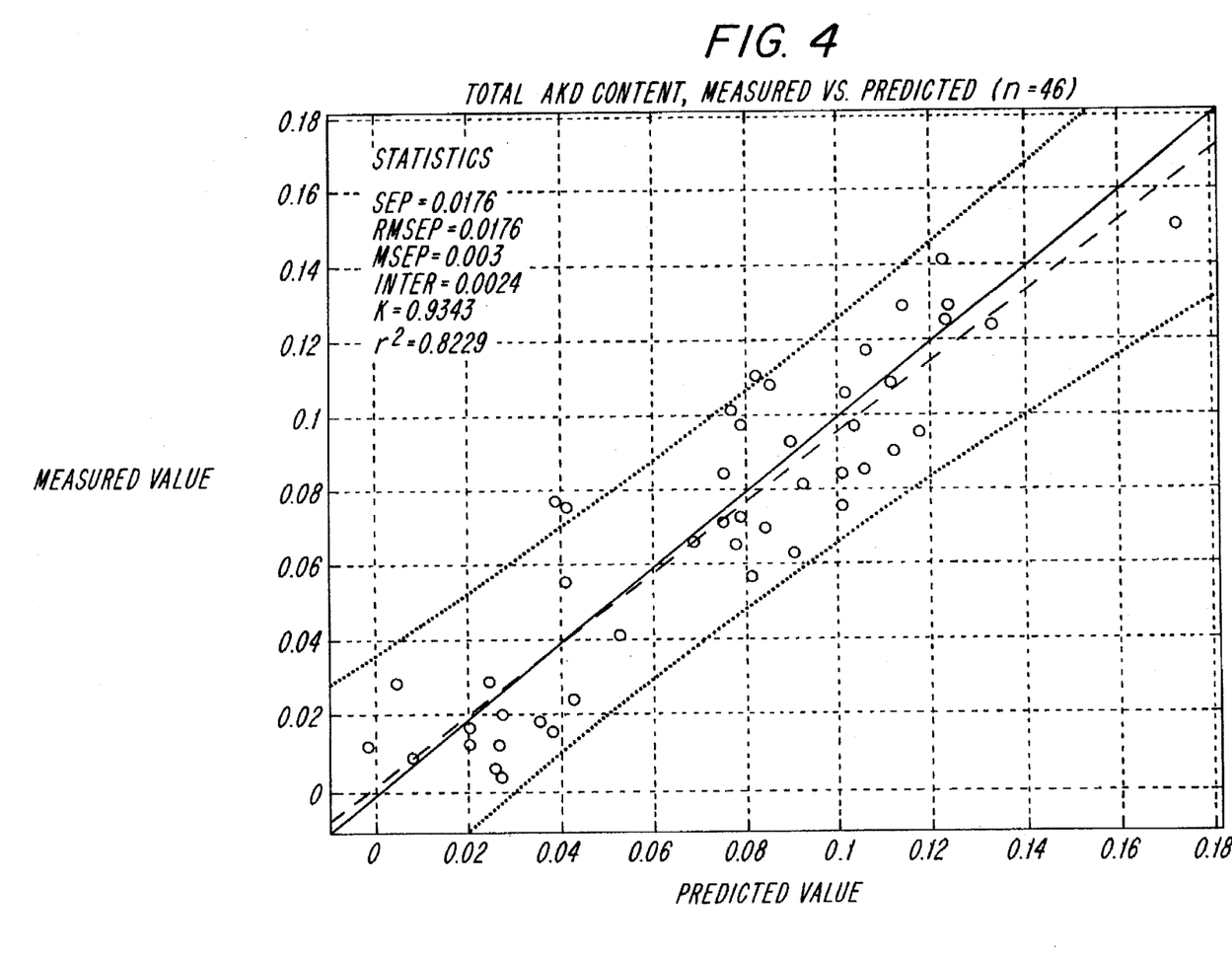
Figure 5:
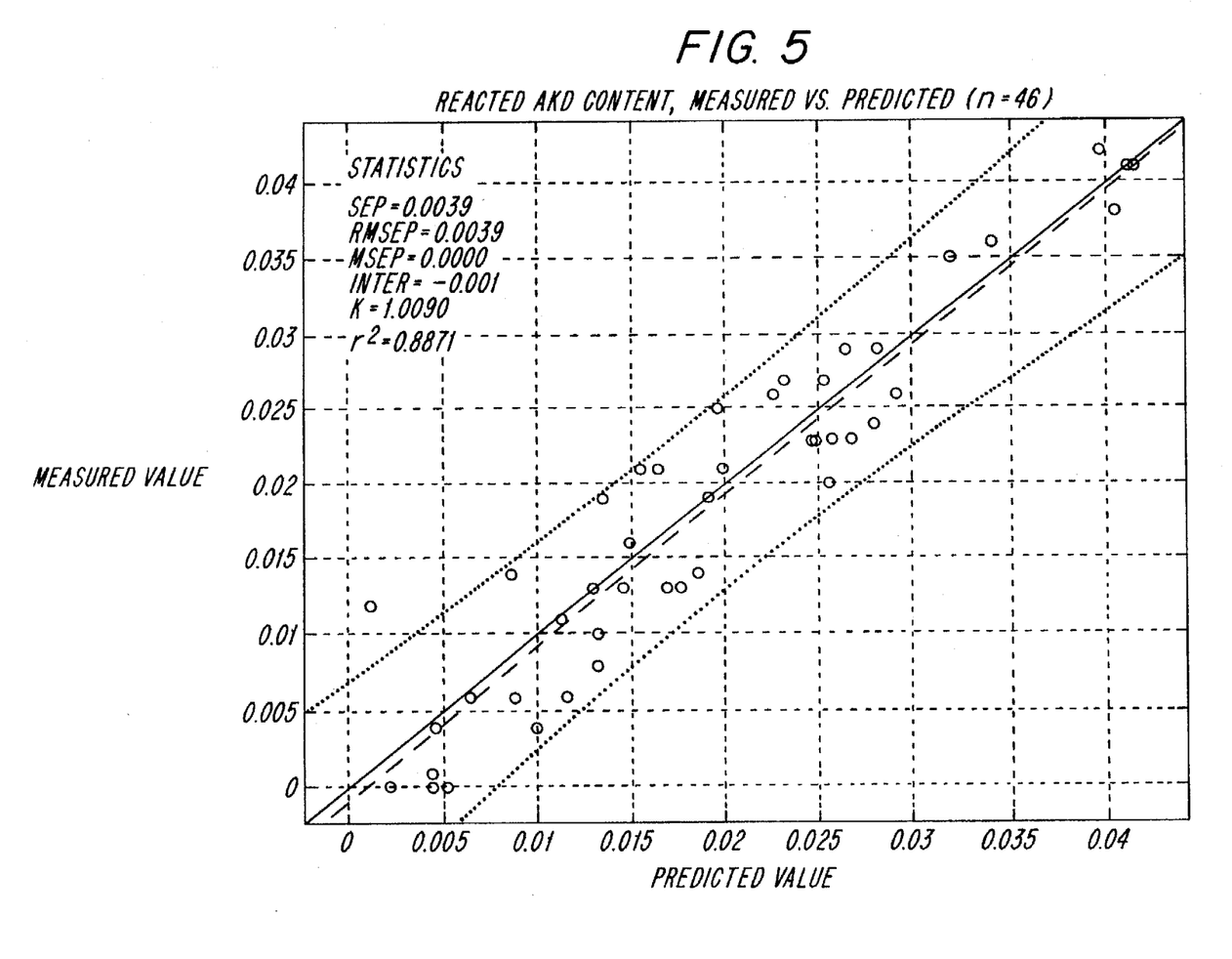

Accordingly, FIG. 1 represents the measured vs. predicted nitrogen content (in %) of 20 samples of bleached paper;

FIG. 2 represents the measured vs. predicted nitrogen in % of 37 samples of unbleached paper;

FIG. 3 represents the measured vs. predicted total nitrogen in % of 51 samples of unbleached paper;

FIG. 4 represents the measured vs. predicted total retained amount of AKD in % of 46 samples of paper;

FIG. 5 represents the measured vs. predicted total amount of reacted AKD in % of 46 samples of paper.

In some of the above mentioned figures and tables are also specified the unadjusted correlation coefficient ($r^2$), SEP (in kNm/kg) (Eq. 4, herein below), RMSEP (in kNm/kg) (Eq. 5, herein below), MSEP (in $kN^2m^2/kg^2$), the intercept (INTER) and the slope (K) of the curves.

$$SEP = \sqrt{(n-1)^{-1} \sum_{i=1}^{n} (\hat{c}_i - c_i - \overline{(\hat{c} - c)})^2} \qquad (4)$$

$$RMSEP = \sqrt{MSEP} \qquad (5)$$

(In Eq. 4, n, $\hat{c}$, c, and i respectively have the same meaning as in Eq. 3).

SEP is a good approximation of one standard deviation of the model residue.

Ideally, $r^2$ and k should be as close to 1 as possible; while SEP, RMSEP, MSEP, and the intercept should be as close to 0 as posssible. In view of the values obtained, it will be possible to realize the very good validity and preciseness of the model.

Definitions of the statistical terms as used are given below.

| Symbols | |
|---|---|
| $y_i$ | Scalar y value for the i t:h sample i.e. the true reference analytical results. |
| $\hat{y}$ | The estimated $y_i$ value given by the PLS modelling. |
| $\bar{y}$ | Mean of $y_i$ values. |
| N | The total number of samples used for modelling. |

$r^2$ Correlation coefficient $$r^2 = \left( \frac{\sum_{i=1}^{N} (\hat{y}_i - \bar{y})^2}{\sum_{i=1}^{N} (y_i - \bar{y})^2} \right)$$

$r^2$ determines how well the data are adjusted to the least squares fitted straight line. Thus $r^2=1.00$ indicates that the calibration equation models 100% of the variation within the set of data. If $r^2=0.00$, then there is no correlation.

SEP Standard Error of Prediction $$SEP = \sqrt{\frac{\sum_{i=1}^{N} (\hat{y} - y - \overline{(\hat{y} - y)})^2}{(N-1)}}$$

SEP is a characterisation of the variance attributable to random unexplainable error.

MSEP Mean Square Error of Prediction $$MSEP = \frac{\sum_{i=1}^{N} (y - \hat{y})^2}{N}$$

MSEP is the average squared differences between actual and predicted values. i.e. for a set of objects not present in the calibration. In the literature MSEP is also referred to as PRESS (Predicted Residual Error Sum of Squares)

RMSEP Root Mean Square Error of Prediction.

$$RMSEP = \sqrt{MSEP}$$

Transforms the MSEP into the original measured unit.

The advantage of the novel method of quantifying the amounts of reacted and/or retained chemicals of pulp and paper using chemometrics thus should be readily apparent. Indeed, a wide variety of paper chemicals, may be determined using the same calibration set. The invention thus provides a method whereby the quantifying of the amounts of reacted and/or retained performance chemicals of pulp and paper during the production process can be performed in a very rapid and precise way on any type of pulp and paper.

We claim:

1. A method for quantifying the amounts of performance chemicals selected from the group consisting of wet strength agents, starches and retention agents, hydrophobic agents and debonding agents, reacted or retained with the cellulose fibers in fluff pulp or paper, which method comprises (I) developing a calibration model by (I.a) registering absorption, reflectance or emission spectral raw data of reference samples of paper or pulp containing known amounts of said performance chemicals to develop a learning set;

(I.b) processing the spectral raw data from the registered spectra to reduce noise and adjust for drift and diffuse light scatter;

(I.c) performing a data analysis on the learning set in which the processed spectral data of the reference samples are transferred into latent variables based on principal component analysis, and applying chemometric techniques on the latent variables in order to find the mathematical expression of the calibration model; and (II) registering absorption, reflectance or emission spectral raw data of a sample of fluff paper or pulp containing unknown amounts of chemicals, processing the spectral raw data as according to (I.b); transferring the processed spectral data into latent variables as according to (I.c), and applying the developed calibration model on the latent variables in order to determine the unknown amounts of said reacted or retained performance chemicals.

2. A method according to claim 1, wherein the recording of the absorption, reflectance or emission spectra is performed in the wavelength range of 200 nm to 400 µm.

3. A method according to claim 1, wherein the spectral data processing in (I.b). is performed using the Kubelka-Munk transform:

$$A_{ik} = \frac{(1 - R_{ik})^2}{2R_{ik}} \quad (1)$$

wherein $R_{ik}$ is the apparent absorbance at the wavelength k, $A_{ik}$ is the transformed absorbance at the wavelength k, and the index i represents the sample spectra available.

4. A method according to claim 3, wherein the recording of the absorption, reflectance or emission spectra is performed in the wavelength range of 800 nm to 2500 nm.

5. A method according to claim 1, wherein the spectral data processing in (I.b) is performed using the Multiplicative Scatter Correction:

$$A_{ik} = \frac{R_{ik} - \hat{a}_i}{\hat{b}_i} \quad (2)$$

wherein $R_{ik}$ is the apparent absorbance at the wavelength k, $A_{ik}$ is the transformed absorbance at the wavelength k, $\hat{a}_1$ is the least squares estimation of the intercept parameter, and $\hat{b}_1$ is the least squares estimation of the slope parameter, the index i representing the sample spectra available, and the index k representing the available wavelengths.

6. A method according to claim 1, wherein the spectral data processing in (I.b) is performed by use of the Fourier transformation.

7. A method according to claim 1, wherein the spectral data processing in (I.b) is performed by use of up to the fourth order derivatives.

8. A method according to claim 1, wherein the spectral data processing in (I.b) is performed by use of the Standard Normal Variate transformation.

9. A method according to claim 1, wherein the data analysis is performed by the use of the Principal Components Regression technique.

10. A method according to claim 1, wherein the data analysis is performed by the use of the Partial Least Squares technique.

11. A method according to claim 1 for quantification of the nitrogen content of reacted or retained amounts of performance chemicals containing nitrogen.

12. A method according to claim 1 for quantification of reacted or retained amounts of alkyl ketene dimer and rosin.

13. A method according to claim 1 for quantification of reacted or retained amounts of alkylene succinic acid and alkyl carbamoyl chloride.

14. A method according to claim 1 for quantification of retained amounts of quaternary fatty amines and fatty amine oxides.

15. A method for maintaining a process control program wherein the amounts of reacted or retained paper and pulp performance chemicals selected from the group consisting of wet strength agents, starches and retention agents, hydrophobic agents and debonding agents are quantified in fluff paper or pulp to detect any change thereof and provide control input in order to assure optimum dosage levels for the performance chemicals, whereby a method as defined in claim 1 is used.

* * * * *

UNITED STATES PATENT AND TRADEMARK OFFICE
CERTIFICATE OF CORRECTION

PATENT NO. : 5,680,320
DATED : October 21, 1997
INVENTOR(S) : Helmer et al.

It is certified that error appears in the above-identified patent and that said Letters Patent is hereby corrected as shown below:

Claim 1, at column 12, line 67, "paper or pulp" should read --fluff pulp or paper--.

Claim 1, at column 13, line 13, "fluff paper or pulp" should read --fluff pulp or paper--.

Claim 15, at column 14, lines 37-38, "fluff paper or pulp" should read --fluff pulp or paper--.

Signed and Sealed this

Ninth Day of March, 1999

*Attest:*

Q. TODD DICKINSON

*Attesting Officer*    Acting Commissioner of Patents and Trademarks